US00PP35611P2

(12) United States Plant Patent
Couturieux

(10) Patent No.: US PP35,611 P2
(45) Date of Patent: Jan. 30, 2024

(54) ***HYDRANGEA* PLANT NAMED 'COUHACINQ'**

(50) Latin Name: ***Hydrangea* x *paniculata***
Varietal Denomination: COUHACINQ

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 0 days.

(21) Appl. No.: 18/115,273

(22) Filed: Feb. 28, 2023

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./226, 250
See application file for complete search history.

(56) References Cited

PUBLICATIONS

Van Vliet New Plants 2022/2023. https://newplants.nl/uploads/catalog-2022-small.pdf. 6 pages (Year: 2022).*
CPVO Application Consultation for 20230293, 'Couhacinq'. https://online.plantvarieties.eu/publicConsultationDetails?registerId=20230293&denomination=couhacinq (Year: 2023).*

* cited by examiner

*Primary Examiner* — Karen M Redden
(74) *Attorney, Agent, or Firm* — Cassandra Bright

(57) ABSTRACT

A new and distinct cultivar of *Hydrangea* plant named 'COUHACINQ' is disclosed, characterized by globular to conical-shaped panicles with flowers that age from greenish-white, to white, to light pink to dark red. Plants have compact habits, brown immature stems, and dark green foliage. The new variety is a *Hydrangea*, typically produced as an outdoor ornamental plant.

4 Drawing Sheets

Latin name of the genus and species: *Hydrangea* x *paniculata*.

Variety denomination: 'COUHACINQ'.

BACKGROUND OF THE INVENTION

The new cultivar is a product of a planned breeding program conducted by the inventor in Vosges, France. The objective of the breeding program was to produce new *Hydrangea* varieties with compact plant habits and panicles that age to vivid dark pink to red. The crossing resulting in the new variety was made during 2010.

The seed and pollen parents cannot be identified as seed was bulk collected.

The new variety was found and selected by the inventor in 2012 at the same nursery in Vosges, France. Asexual reproduction of the new cultivar 'COUHACINQ' was first performed during 2012 in Vosges, France, by softwood cuttings. Through subsequent propagation, multiple additional generations have been reproduced, having shown that the unique features of this cultivar are stable and reproduced true to type.

SUMMARY OF THE INVENTION

The cultivar 'COUHACINQ' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COUHACINQ'. These characteristics in combination distinguish 'COUHACINQ' as a new and distinct *Hydrangea* cultivar:

1. Globular to conical-shaped panicles.
2. Flowers age from greenish-white, to white, to light pink, medium pink and finally dark pink.
3. Brown stem color on new growth.
4. Dark green foliage.

PARENT COMPARISON

Comparison cannot be made to the parent varieties are they cannot be identified.

COMMERCIAL COMPARISON

Plants of the new cultivar *Hydrangea* 'COUHACINQ' can be compared to the commercial variety *Hydrangea* 'RENBA', U.S. Plant Pat. No. 28,509. Plants of 'COUHACINQ' are similar to plants of 'RENSBA' in most horticultural characteristics, however, plants of 'COUHACINQ' differ in the following:

1. Flower panicles of the new variety are more globular than the conical flower panicles of this comparator.
2. Plants of the new variety are more compact and bushy compared to the larger, more vigorous plants of this comparator.

BRIEF DESCRIPTION OF THE PHOTOGRAPHS

The accompanying photographs illustrate typical plants of 'COUHACINQ' grown outdoors in Vosges, France. Plants are approximately 2-3 years old, grown in the ground in a trial field. The Figures illustrate inflorescences of the new variety at different stages of maturity. The photographs were taken using conventional techniques and although colors may appear different from actual colors due to light reflectance it is as accurate as possible by conventional photographic techniques.

DETAILED BOTANICAL DESCRIPTION

Figure 1:
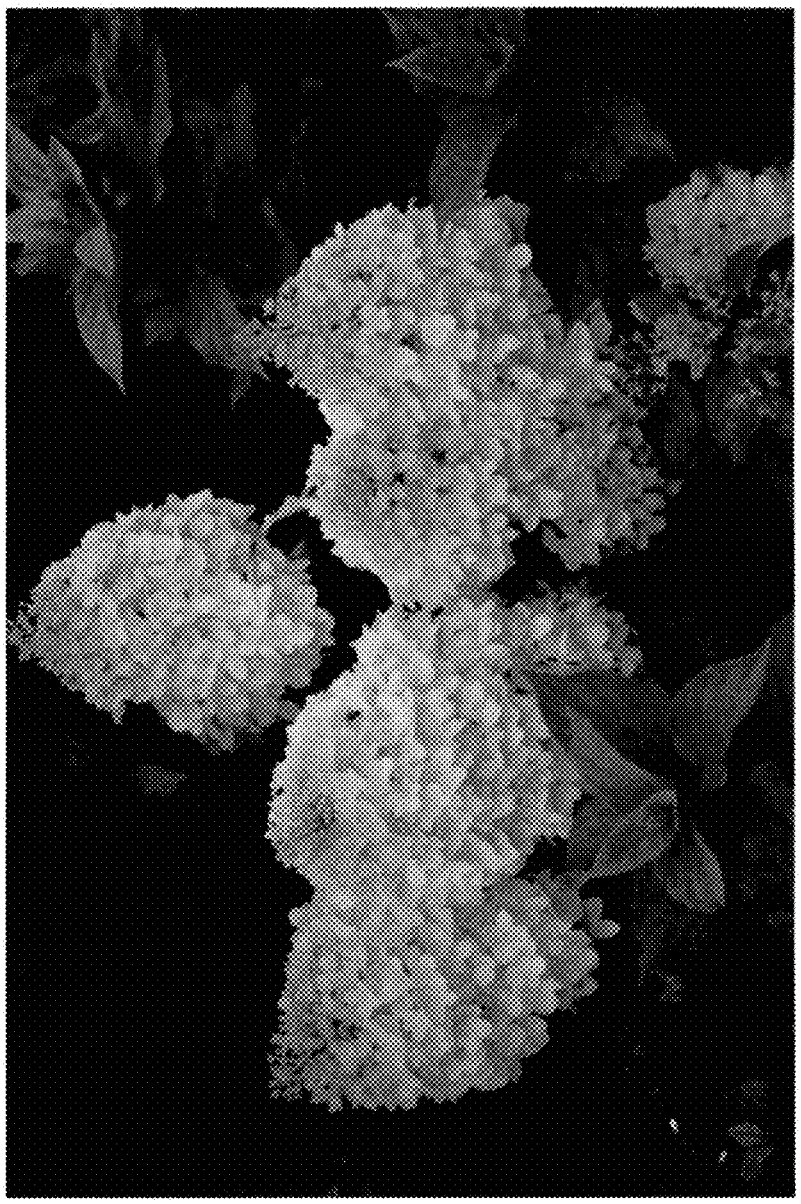
FIG. 1 illustrates a plant of 'COUHACINQ' with inflorescences in the earliest stage of maturity, taken during July 2017.
Figure 2:
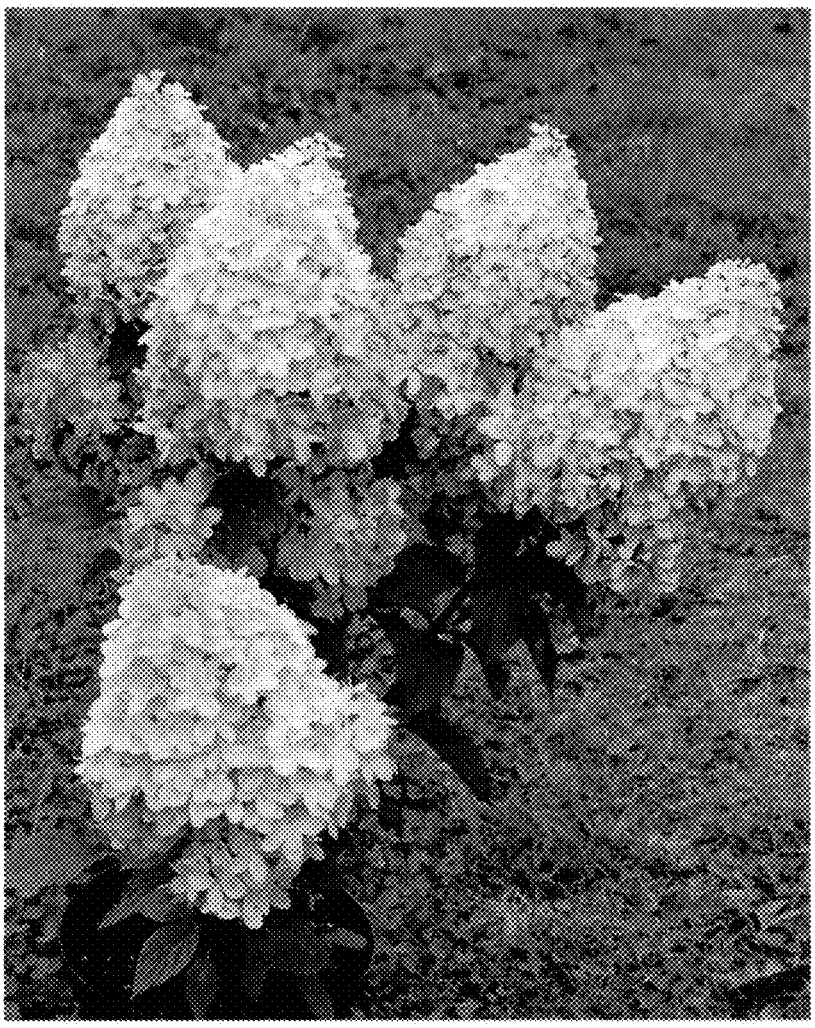
FIG. 2 illustrates a plant of 'COUHACINQ' with inflorescences in the semi-mature stage of maturity, with pink coloration just beginning to show. This photo was taken in mid-August.
Figure 3:
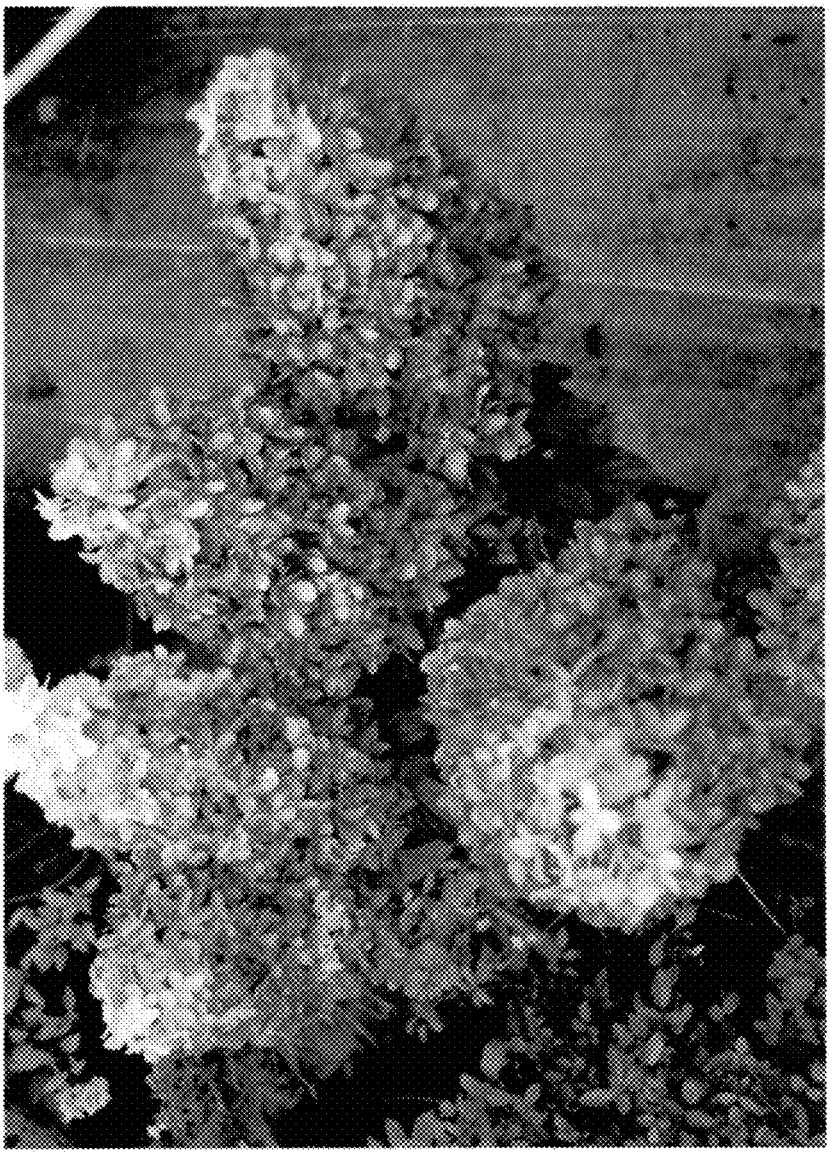
FIG. 3 illustrates in full color a close up of a mature inflorescence of 'COUHACINQ', with the photo taken during the first week of September.
Figure 4:
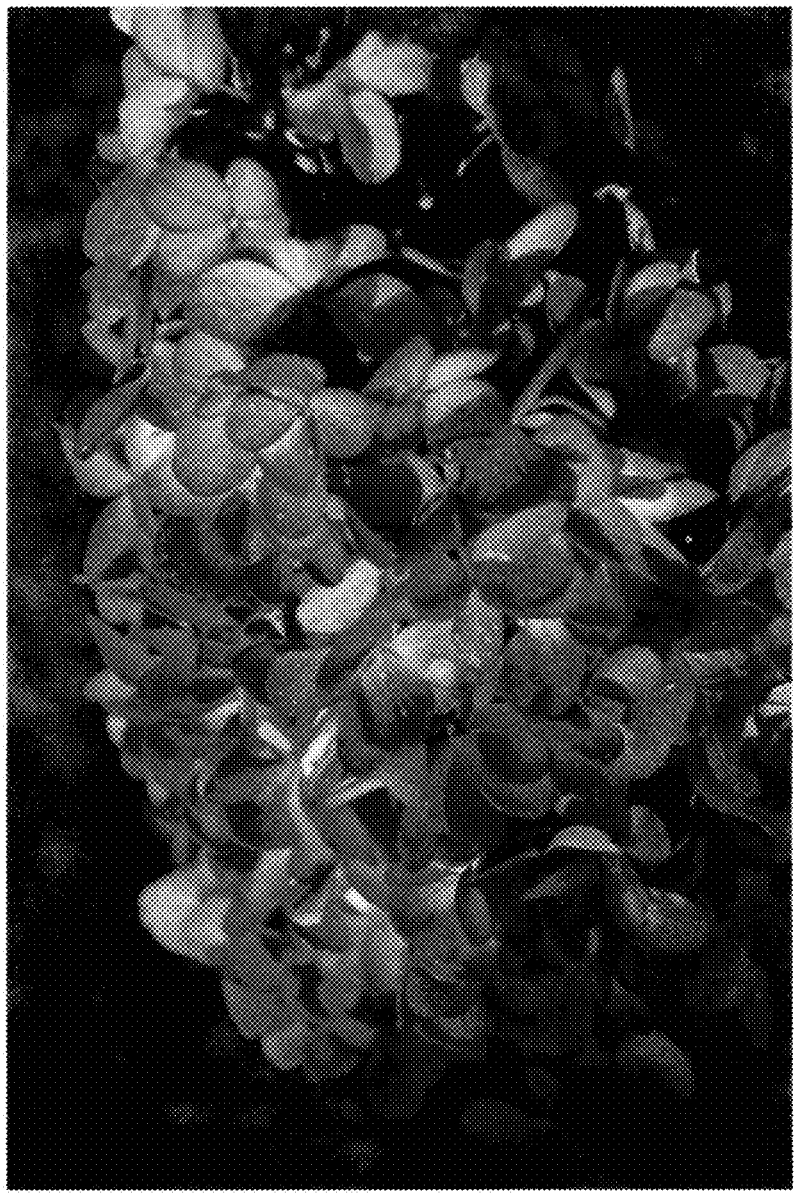
FIG. 4 illustrates in full color a close up of an inflorescence of 'COUHACINQ' at the most mature stage, with the photo taken at the end of September.

In the following description, color references are made to The Royal Horticultural Society Colour Chart 2007, except where general terms of ordinary dictionary significance are used. The following observations and measurements describe 'COUHACINQ' plants grown in a ploy-greenhouse in Vosges, France. The plants were about 2 to 3 years old. Temperatures ranged from 5° C. to 10° C. at night to 18° C. to 27° C. during the day. No artificial light, photoperiodic treatments were given to the plants. Measurements and numerical values represent averages of typical plant types.

Botanical classification: *Hydrangea* x *paniculata* 'COUHACINQ'.

PROPAGATION

Typical method: Softwood cuttings.
Root initiation: 20 days at 20° C. during summer.
Time to produce rooted cutting: About 2 months at 20° C. during summer.
Roots: Dense, freely branching, fibrous, thick to thin. Creamy white to brown in color, not accurately measured with R.H.S. chart.

PLANT

Growth habit: Upright, and somewhat outwards, compact.
Height: 70 to 80 cm.
Plant spread: 60 cm.
Pot size of plant described: 2 gallon container.
Age of plant described: Approximately 2 years.
Growth rate: Good.
Plant vigor: Moderately vigorous.
Stem:
- *Branching*.—Basal.
- *Number of lateral branches*.—8.
- *Shape*.—Rounded.
- *Color*.—RHS Brown 200B with Grey-Brown 199C lenticels.
- *Length*.—50 cm.
- *Width*.—7 mm.
- *Aspect*.—60 to 70°.
- *Strength*.—Strong with some flexibility.
- *Pubescence*.—None.
- *Internode length*.—6 cm to 10 cm.

FOLIAGE

Leaf:
- *Arrangement*.—Whorl (3 leaves equally spaced around each node).
- *Shape*.—Broad elliptic.
- *Length*.—10 cm.
- *Width*.—5 cm.
- *Apex*.—Acuminate.
- *Base*.—Obtuse.
- *Margin*.—Serrulate.
- *Texture of top surface*.—Roughly textured with coarse, bristly hairs.
- *Texture of bottom surface*.—Roughly textured with coarse, bristly hairs and pronounced venation.
- *Pubescence*.—Yes, upper and lower surfaces.
- *Color*.—Young foliage upper side: RHS Green 136A. Young foliage under side: RHS Green 136B. Mature foliage upper side: RHS Green 139A Mature foliage, under side: RHS Green 137A.

Venation:
- *Type*.—Pinnate.
- *Color*.—Upper side: RHS Green 139C. Under side: Green 139B.

Petiole:
- *Length*.—4 cm.
- *Width*.—4 mm.
- *Color*.—RHS Brown 200B.
- *Texture*.—Lightly pubescent.

INFLORESCENCE

Natural flowering season: Summer.
Inflorescence type: Mophead.
Panicle:
- *Shape*.—Conical to globular.
- *Height*.—15 to 24 cm.
- *Diameter*.—12 to 18 cm.

Fragrance: Faintly sweet.
Sterile flowers:
- *Flowers per inflorescence*.—200 to 300.
- *Aspect*.—Outward.
- *Shape*.—Cruciform/stellate.
- *Length*.—2 cm.
- *Diameter*.—3 cm.
- *Persistent or self-cleaning*.—Persistent.

Bud:
- *Length*.—3 mm.
- *Diameter*.—3 mm.
- *Shape*.—Obovate.
- *Color*.—RHS Yellow-Green 145C.

Petals:
- *Number per flower*.—3 to 4.
- *Shape*.—Elliptic.
- *Tip*.—Acute.
- *Base*.—Truncate.
- *Margin*.—Entire.
- *Length*.—3 mm.
- *Width*.—2 mm.
- *Texture*.—Upper side: Smooth. Under side: Smooth.
- *Color*.—When Opening, Upper side: RHS Green 145D. When Opening, Under side: RHS Green 145D. Fully Opened, Upper side: RHS White N155A. Fully Opened, Under side: RHS White N155A.

Sepal:

*Number per flower.*—4 to 5.
*Shape.*—Ovate.
*Tip.*—Broad rounded.
*Base.*—Truncate.
*Margin.*—Entire.
*Length.*—1.8 cm.
*Width.*—8 mm.
*Texture.*—Upper side: Smooth. Under side: Smooth.
*Color.*—Earliest Stage, Upper side: RHS Green-White 157A. Earliest Stage, Under side: RHS Green-White 157A. Semi-mature, Upper side: RHS White 155A. Lightly tinged overall Yellow 4D, margin begins to be flushed Red-Purple 72C. Semi-mature, Under side: RHS White N155A. Lightly tinged overall Yellow 4D, margin begins to be flushed Red-Purple 70D. Mature, Upper side: RHS Yellow 4D heavily or completely flushed 61C. Mature, Under side: RHS Yellow 4D heavily flushed 61C. Mature before senescence Upper side: RHS Red 53C, veins Red-Purple 59C, base yellow 5D. Mature before senescence, Under side: RHS Red 53D, veins Red-Purple 59C, base yellow 4D.

Pedicel:

*Length.*—1.5 cm.
*Diameter.*—2 mm.
*Angle.*—45°.
*Strength.*—Good, flexible.
*Texture.*—Lightly pubescent.
*Color.*—RHS Yellow 4D.

Fertile flowers: Absent or highly reduced and inconspicuous.

REPRODUCTIVE ORGANS

Sterile flower:

Stamens:

*Number.*—About 8.
*Filament color.*—RHS White 155A.
*Filament length.*—3 mm.

Anthers:

*Length.*—1 mm.
*Shape.*—Rounded.
*Color.*—RHS Yellow-White 158A.
*Pollen.*—Moderate.
*Pollen color.*—RHS Yellow-White 158C.

Pistil:

*Number.*—1.
*Length.*—1 mm.

Stigma:

*Shape.*—Bi-lobed.
*Color.*—RHS Yellow-White 158A.
*Style length.*—0.5 mm.
*Style color.*—RHS Yellow-White 158C.

OTHER CHARACTERISTICS

Disease resistance: Neither resistance nor susceptibility to the normal diseases and pests of *Hydrangea* has been observed.

Drought tolerance and cold tolerance: The new cultivar can tolerate cold temperatures to approximately −31° C. and tolerates an upper temperature range to at least 38° C.

Fruit/seed production: Not observed to date.

What is claimed is:

1. A new and distinct cultivar of *Hydrangea* plant named 'COUHACINQ' as herein illustrated and described.

* * * * *